United States Patent [19]

Holland et al.

[11] 4,212,993

[45] Jul. 15, 1980

[54] 16-SUBSTITUTED PROSTAGLANDINS

[75] Inventors: George W. Holland; Perry Rosen, both of North Caldwell, N.J.

[73] Assignee: Hoffmann-La Roche Inc., Nutley, N.J.

[21] Appl. No.: 27,589

[22] Filed: Apr. 6, 1979

Related U.S. Application Data

[62] Division of Ser. No. 813,068, Jul. 5, 1977, Pat. No. 4,163,016.

[51] Int. Cl.$^2$ ............................................. C07C 177/00
[52] U.S. Cl. ..................................... 562/503; 560/121
[58] Field of Search .......................... 560/121; 562/503

[56] References Cited

U.S. PATENT DOCUMENTS 4,053,467  10/1977  Kao et al. ............................. 542/426

*Primary Examiner*—Robert Gerstl
*Attorney, Agent, or Firm*—Jon S. Saxe; Bernard S. Leon; William H. Epstein

[57] ABSTRACT

The 16-substituted 15-hydroxy prostaglandins which are saturated at the 13-position and the 16-substituted-15-keto prostaglandins, said prostaglandins being useful as antisecretory agents, blood pressure lowering agents, anti-ulcerogenic agents and antihypertensive agents.

4 Claims, No Drawings

16-SUBSTITUTED PROSTAGLANDINS

CROSS REFERENCE TO RELATED APPLICATION

This is a division of application Ser. No. 813,068 filed July 5, 1977 now U.S. Pat. No. 4,163,016.

This application is related to U.S. patent application Ser. No. 745,257 filed Dec. 8, 1976 now U.S. Pat. No. 4,112,225.

SUMMARY OF INVENTION

In accordance with this invention, it has been discovered that compounds selected from the group consisting of compounds of the formula:

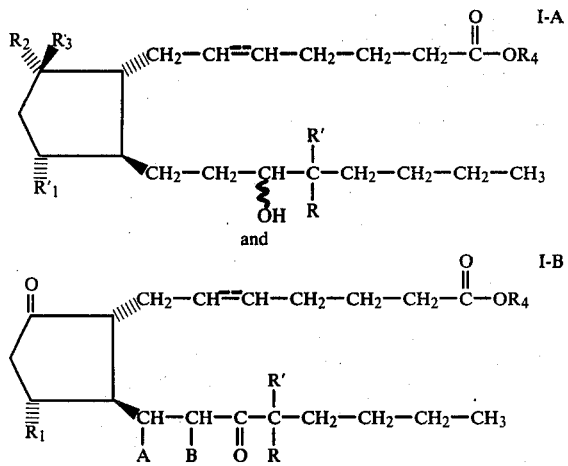

wherein A and B are individually hydrogen or form a carbon to carbon bond; $R_4$ is hydrogen or lower alkyl; $R_2$ is hydroxy, $R_3$ is hydrogen or taken together with $R_2$ forms oxo; $R_1$, and $R_1'$ are hydrogen or lower alkyl; $R'$ is fluoro, lower alkyl or trifluoromethyl; $R$ is hydrogen, fluoro or lower alkyl; and the dotted bond can be optionally hydrogenated with the proviso that when $R_1'$ is hydrogen, the dotted bond is not hydrogenated, and their optical antipodes and racemates thereof are useful as bronchodilators, antisecretory agents, antihypertensives, antiulcerogenic agents and blood pressure lowering agents and for combatting gastrohyperacidity.

The compounds of formula I-A and I-B are prepared in accordance with the invention from compounds of the formula

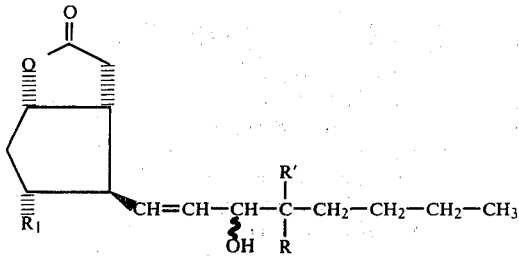

wherein R, R' and $R_1'$ are as above.

The compound of formula II is disclosed in U.S. application 745,257 filed Dec. 8, 1976 (please note Compound VI and Example 8, Example 23, Example 47, Example 53, Example 59, Example 79 and Example 80).

The compound of formula II can also be used to prepare compounds of formula I-A where $R_1'$ is hydrogen and the dotted bond is hydrogenated. These compounds are disclosed in U.S. Pat. No. 4,017,534, Apr. 12, 1974 and U.S. Pat. No. 3,932,463.

DETAILED DESCRIPTION OF THE INVENTION

As used throughout this application, the term "lower alkyl" includes both straight chain and branched chain alkyl groups having from 1 to 7 carbon atoms such as methyl and ethyl. As also used herein, the term "lower alkanoic acids" comprehends an alkanoic acid of 1 to 7 carbon atoms such as formic acid and acetic acid. As further used herein, the term "halogen" or "halo", unless otherwise stated, comprehends fluorine, chlorine, bromine and iodine.

In the process of this invention, all compounds having one or more asymmetric carbon atoms can be produced as racemic mixtures. These racemic mixtures which are obtained can be resolved at the appropriate steps in the process of this invention by methods well known in the art whereupon subsequent products may be obtained as the corresponding optically pure enantiomers. On the other hand, the claimed optically active enantiomer or racemate of formula I-A and I-B may be produced depending upon the optical form of the compound of formula II utilized as a starting material.

In the pictorial representation of the compounds given throughout this application, a thickened taper line (▼) indicates a substituent which is in the beta-orientation (above the plane of the molecule), a dotted line (⫶⫶⫶) indicates a substituent which is in the alpha-orientation (below the plane of the molecule) and a wavy line (∿) indicates a substituent which is in either the alpha- or beta-orientation or mixtures of these isomers. It is to be understood that the pictorial representations of the compounds given throughout the specification are set forth for convenience and are to be construed as inclusive of other forms including enantiomers and racemates and are not to be construed as limited to the particular form shown.

As also used herein, the term "aryl" signifies mononuclear aromatic hydrocarbon groups such as phenyl, tolyl, etc. which can be unsubstituted or substituted in one or more positions with a lower alkylenedioxy, a halogen, a nitro, or a lower alkoxy substituent and polynuclear aryl groups such as naphthyl, anthryl, phenanthryl, azulyl, etc., which can be substituted with one or more of the aforementioned groups. The preferred aryl groups are the substituted and unsubstituted mononuclear aryl groups, particularly phenyl. The term "aryl lower alkyl" comprehends groups wherein aryl and lower alkyl are as defined above, particularly benzyl.

As still further used herein, the term "carboxy protected with a group convertible thereto by hydrolysis" comprehends any conventional organic acid protecting group which can be removed by hydrolysis. The preferred organic acid protecting groups are the esters. Any conventional ester that can be hydrolyzed to yield the acid can be utilized as the protecting group. Exemplary esters useful for this purpose are the lower alkyl esters, particularly methyl and ethyl esters, the aryl esters, particularly phenyl ester and the aryl lower alkyl esters, particularly benzyl ester.

As used herein, the term "hydrolyzable ester or ether group" designates any ester or ether which can be hydrolyzed to yield the hydroxy group. Exemplary ester groups useful for this purpose are those in which the acyl moiety is derived from a lower alkanoic, an aryl lower alkanoic, phosphoric, carbonic or a lower alkane dicarboxylic acid. Among the acids which can be utilized to form such ester groups are the acid anhydrides and the acid halides, preferably chlorides or bromides, with the lower alkanoic acid anhydrides, e.g., acetic anhydride and caproic anhydride, the aryl lower alkanoic acid anhydrides, e.g., benzoid acid anhydrides, lower alkane dicarboxylic acid anhydrides, e.g., succinic anhydride, and chloroformates, e.g., trichloroethylchloroformate, being preferred. A suitable ether protecting group is, for example, the tetrahydropyranyl ether or 4-methoxy-5,6-dihydro-2H-pyranyl ether. Others are arylmethyl ethers such as benzyl, benzylhydryl, or trityl ethers or alpha-lower alkoxy lower alkyl ethers, for example, methoxymethyl or allylic ethers, or trialkyl silyl ethers such as trimethyl silyl ether or dimethyl-tert-butyl silyl ethers.

The compounds of formula I-A and their optical antipodes and racemates are active as anti-secretory, blood pressure lowering and anti-ulcerogenic agents and antihypertensive agents. The compounds of formula I-B and their optical antipodes and racemates where A and B form a double bond, i.e. compounds of the formula:

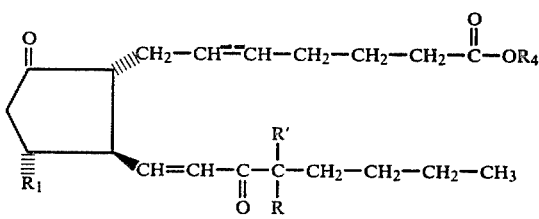

I-B₁ wherein $R_1$, R, R' and $R_4$ are as above and the dotted bond can be optically hydrogenated
are also active as anti-secretory agents, blood pressure lowering agents, and antiulcerogenic agents.

The compounds of formula I-B and their optical antipodes and racemates where A and B are hydrogen, i.e. compounds of the formula:

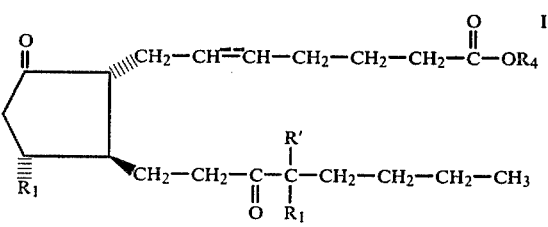

I-B₂ wherein R, R', $R_1$ and $R_4$ are as above, and the dotted bond can be optionally hydrogenated
are useful as anti-secretory and anti-ulcerogenic agents.

That the compounds of this invention are active as blood pressure lowering agents can be seen from the administration of nat. 11R-methyl-16R-fluoro-9,15-dioxo-prosta-(Z)-5-(E)-13-dienoic acid to rats by the following test:

Charles River male rats weighing 170-210 grams are used in the present study. DOCA-Na hypertension is induced in these rats by unilateral nephrectomy followed by subcutaneous implantation of a 25 mg deoxycorticosterone acetate pellet. Animals are placed in individual cages and receive 0.9% by weight sodium chloride aqueous solution and rat chow diet ad libitum. Two weeks are allowed to elapse from the time of surgery for development of hypertension, i.e. systolic blood pressure above 150 mm Hg. Systolic blood pressure is measured indirectly from the tail of unanesthetized rats (restrained in holders heated for 5-10 minutes at 37°-38° C.) using a pneumatic pulse transducer (piezolelectric crystal and occluding cuff). The transducer and occluding cuff are coupled to a two-channel recorder. Control readings are taken prior to drug and at 1, 3, 6, 24, 48 and 72 hours post administration of drug. All drugs are prepared fresh in a mixture of tris(hydroxymethyl)amino methane in 95% ethanol (5% wt/V) and orally administered to rats. The placebo that was used was the mixture tris(hydroxymethyl)amino methane in ethanol without drug.

The results of this test were as follows:

| Dose (mg/kg p.o.) | N | Oral Activity of Prostaglandin Analogs on Systolic Blood Pressure in the DOCA-Na Hypertensive Rat Model | | | | | | |
|---|---|---|---|---|---|---|---|---|
| | | Systolic Blood Pressure Time(hours) | | | | | | |
| | | 0 | 1 | 3 | 6 | 24 | 48 | 72 |
| 1.0 | 6 | 196 ± 6 | 200 ± 6 | 205 ± 6 | 203 ± 8 | 199 ± 6 | — | — |
| 5.0 | 6 | 197 ± 3 | 175 ± 2* | 167 ± 4* | 166 ± 3* | 163 ± 4* | 171 ± 7* | 193 ± 6 |

*p <.05

That the compounds of this invention are active as anti-secretory and antiulcerogenic agents can be seen by administering the following compounds: Compound A=nat 11R-methyl-16R-fluoro-15R-hydroxy-9-oxo-prost-(Z)-5-enoic acid. Compound B=nat 11R-methyl-16R-fluoro-9,15-dioxo-prost-(Z)-5-enoic acid to rats by the following test:

The compounds were tested as gastric secretory depressants in the unanesthetized rat with acute gastric fistula. On the day prior to the experiment, fasted female rats (average weight 250 g) were surgically catheterized in the inferior vena cava (for the constant infusion of saline and administration of compounds), the common bile duct (to divert bile and pancreatic secretions which may reflux causing contamination of gastric contents), the forestomach (for infusion of a small volume of water during the experiment) and the glandular stomach (for the collection of gastric contents and their continuous monitoring by means of a pH microelectrode). On the day of the experiment, water infusion through the stomach was begun for a period of 60 minutes prior to drug administration. During this baseline period, the pH of the secretory flow was about 1.5 for each animal. Individual samples were collected at 10-minute intervals during this baseline period to monitor the pH. The compound dissolved in saline was administered intravenously (i.v.),16 μg/Kg i.v., after this baseline period and samples were continuously collected for 60 minutes. The samples of gastric contents were subsequently assayed for pH, volume, total acid content (μEq/ml) and total acid output for 10 minutes (μEq/10 minutes). The results for this test are as follows:

| | ANTI-SECRETORY ACTIVITY OF PROSTAGLANDIN ANALOGS IN THE CONSCIOUS RAT WITH ACUTE GASTRIC FISTULA | | | | | | | |
|---|---|---|---|---|---|---|---|---|
| | Compound A[e] | | | | Compound B[e] | | | |
| Minutes after | | | Acid | | | | Acid | |
| Administration | pH[a] | Volume[b] | Conc.[c] | Output[d] | pH[a] | Volume[b] | Conc.[c] | Output[d] |
| 10 | 5 | 0 | 0 | 4 | 2 | 9 | 33 | 40 |
| 20 | 6 | 22 | 17 | 2 | 30 | 6 | 22 | |
| 30 | 4 | 58 | 20 | 33 | 2 | 4 | 11 | 15 |
| 40 | 5 | 21 | 23 | 26 | 2 | 11 | 2 | 14 |
| 50 | 9 | 9 | 38 | 43 | 2 | 16 | 15 | 20 |
| 60 | 9 | 0 | 22 | 25 | 5 | 35 | 19 | 48 |
| N[f] = | | | 3 | | | | 2 | |

[a] % Increment over baseline.
[b] % Inhibition.
[c] % Inhibition (calculated from μ Eq/ml of total acid concentration).
[d] % Inhibition (calculated from μ Eq/10 min period of total acid output).
[e] Rounded figures: 0 = No effect, or increase in the hydrogen ion concentration.
[f] Number of rats tested.

The compounds of formula I-A and I-B can be used by the pharmaceutical and veterinary arts in a variety of pharmaceutical or veterinary preparations. In these preparations, the new compounds are administerable in the form of tablets, pills, powders, capsules, injectables, solutions, suppositories, emulsions, dispersions, feed pre-mixes and in other suitable forms. The pharmaceutical or veterinary preparations which contain the compound of formula I are conveniently admixed with a non-toxic pharmaceutical organic carrier or a non-toxic pharmaceutical inorganic carrier. Typical of pharmaceutically acceptable carriers are, for example, water, gelatin, lactose, starches, magnesium stearate, talc, vegetable oils, polyalkylene glycols, petroleum jelly and other conventionally employed pharmaceutically acceptable carriers. The pharmaceutical preparations may also contain non-toxic auxiliary substances such as emulsifying, preserving and wetting agents and the like, as for example, sorbitan monolaurate, triethanol amine oleate, polyoxyethylene sorbitan, dioctyl sodium sulfosuccinate and the like.

The daily dose administered for the compounds will, of course, vary with the particular novel compounds employed because of the very potency of the compounds, the chosen route of administration and the size of the recipient. The dosage administered is not subject to definite bounds but it will usually be in effective amounts of the pharmacologically function of the prostaglandin. Representative of a typical method for administering the prostaglandin compounds of formula I is by the injectable type administration route. By this route, a sterile solution containing the prostaglandin of formula I can be administered intraveneously at the rate of 0.1 microgram to 0.30 micrograms per day per kilogram of body weight. The compounds to be administered by the injectable route is in a form suitable for injection such as mixed with a sterile aqueous solution having incorporated therein an agent that delays adsorption such as aluminum monostereate and the like.

For administering the compounds of formula I to domestic animals or laboratory animals, the compounds are prepared in the form of a food pre-mix such as mixing with dried fish meal, oatmeal and the like and the prepared pre-mix is added to a regular feed thereby administering the compound to the domestic or laboratory animal in the form of a feed.

Depending upon the particular form of the compound of formula I desired, the compound of formula II which is utilized as a starting material can be either a racemate or can be in the form of its optical antipodes.

The compound of formula I-A wherein $R_2$ is hydroxy and $R_3$ is hydrogen and the dotted bond is not hydrogenated, i.e. a compound of the formula:

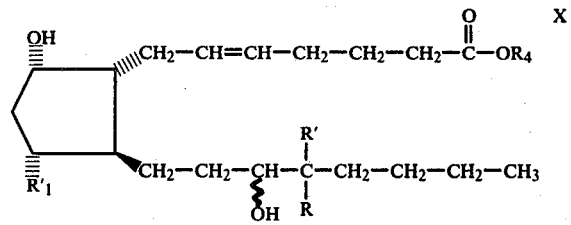

wherein $R_1'$, $R_4$, R and R' are as above
can be prepared from the compound of formula II via the following intermediates

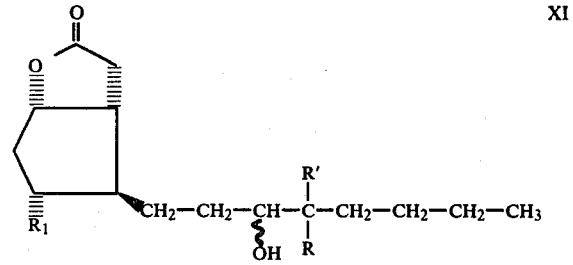

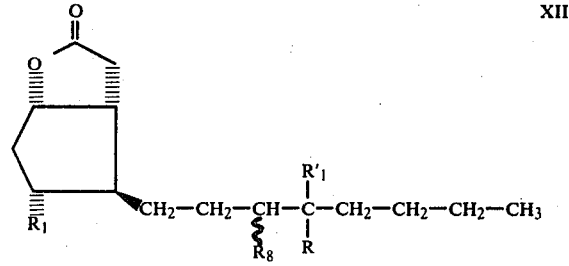

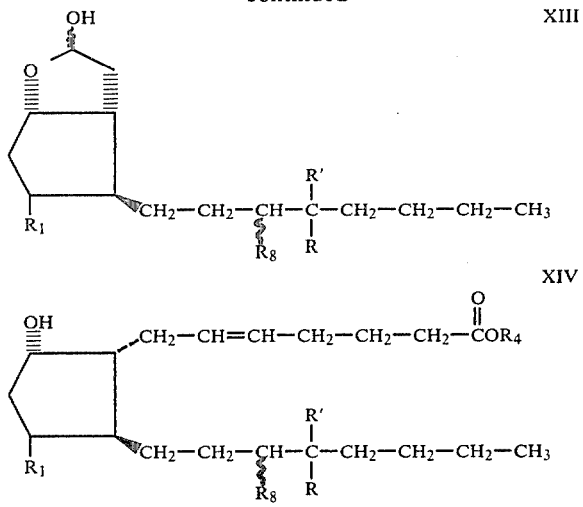

XIII

XIV wherein R', R, R$_1$ and R$_4$ are as above and R$_8$ is a hydroxy protected with a hydrolyzable ether or ester group.

In the first step of this reaction, the compound of II is converted to a compound of XI. This reaction is carried out by hydrogenation. Any conventional method of hydrogenation such as catalytic hydrogenation can be utilized to carry out this reaction. Among the preferred methods of hydrogenation is by reacting these compounds with hydrogen in the presence of a catalyst such as platinum or oxides of platinum. Any conventional hydrogenation catalysts can be utilized for carrying out this conversion. The conditions utilized in this reaction are the conditions conventional for hydrogenation reaction.

The compound of formula XI is converted to the compound of formula XII by esterifying or etherifying the free hydroxy group with a hydrolyzable ether or ester protecting group. This esterification or etherification can be carried out by conventional esterification or etherification procedures. Among the preferred hydrolyzable ester groups are the the lower alkanoyloxy with acetoxy being especially preferred. Among the preferred hydrolyzable ether groups are included tetrahydropyranyl.

The compound of formula XII is converted to the compound of formula XIII by treating the compound of formula XIII with a reducing agent. In carrying out this reaction, any conventional reducing agent which will selectively reduce a lactone to a lactol can be utilized. Among the reducing agents are included the hydrides, as well as alkali metal borohydrides, with di-isobutyl aluminum hydride being particularly preferred. Also, this reaction can be carried out utilizing di-(branched chain lower alkyl)boranes such as bis(3-methyl-2-butyl)borane. In carrying out this reaction, temperature and pressure are not critical and the reaction can be carried out at room temperature and atmospheric pressure or elevated or reduced temperatures and pressures. Generally, it is preferred to carry out this reaction at a temperature of from −70° C. to room temperature (20° C.). This reduction reaction can be carried out in the presence of an inert organic solvent. Any conventional inert organic solvents can be utilized in carrying out this reaction. Among the preferred solvents are dimethoxy ethylene glycol, and the ethers such as tetrahydrofuran, diethyl ether and dioxane.

The compound of formula XIV where R$_4$ is hydrogen is obtained from the compound of formula XIII by reacting the compound of formula XIII with phosphonium salts of the formula:

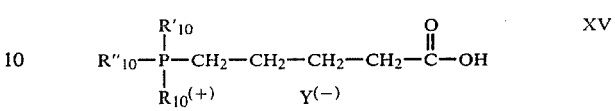

XV wherein R$_{10}$, R$_{10}'$, R$_{10}''$ are aryl or di(lower alkyl)amino and Y is halogen.

In accordance with this invention, it is found that the compounds of the formula XIII will react with the compound of formula XV to produce a compound of formula XIV with a predominately cis double bond at the 5-position of the acid chain in a solvent medium containing hexamethylphosphoramide utilizing sodium bis-trimethylsilylamide as a base. If solvents other than hexamethylphosphoramide or bases other than sodium bis-trimethylsilylamide are utilized, the compound of formula XIV may form in poorer yields. However, conventional inert organic solvents may be mixed with the hexamethylphosphoramide to form the solvent medium in accordance with this invention. If other solvents are utilized, these solvents can be conventional inert organic solvents. On the other hand, the solvent system can contain only the hexamethylphosphoramide. Therefore, this reaction is carried out utilizing hexamethylphosphoramide as the solvent and sodium bis-trimethylsilyl-amide as the base. In carrying out this reaction, temperature and pressure are not critical and this reaction can be carried out at room temperature and pressure. However, if desired, higher or lower temperatures can be utilized. Generally, it is preferred to carry out this reaction at a temperature of from 0° to 50° C.

The compound of formula XIV where R$_4$ is hydrogen can be converted, if desired, to the corresponding compound of formula XIV where R$_4$ is lower alkyl by conventional esterification procedures such as by reacting with diazo-methane.

The compound of formula XIV is converted to the compound of formula X by aqueous acid hydrolysis where the hydroxy group is protected via an ether linkage. Any conventional method of ether hydrolysis can be utilized. Among the preferred methods of ether hydrolysis is by treating the compound of formula XIV with an aqueous inorganic acid. On the other hand, where R$_8$ forms an ester linkage, the hydroxy group can be regenerated by treatment with a base in an aqueous medium. Any conventional method of ester hydrolysis can be utilized in this conversion. Among the preferred bases is aqueous sodium hydroxide. Where R$_8$ forms an ester, basic hydrolysis will also cleave the compound of formula XIV where R$_4$ is lower alkyl to produce a compound of the formula X where R$_4$ is hydrogen. Therefore, if it is desired to produce a compound of formula X where R$_4$ is alkyl, an ether protecting group such as tetrahydropyranyloxy should be utilized in forming the substituent R$_8$.

The compound of formula X or the compound of formula XIV can be converted to a compound of the formula

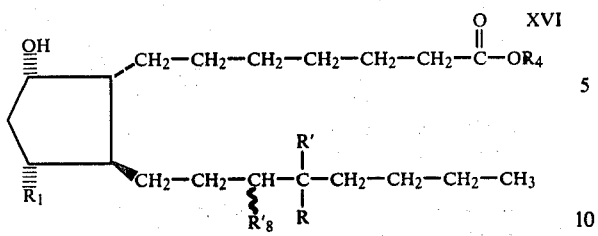

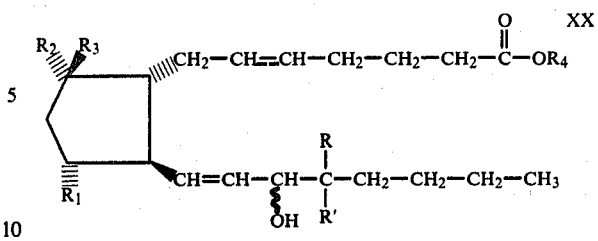

wherein R, R', $R_1$ and $R_4$ are as above; and $R_8'$ is hydroxy or hydroxy protected by a hydrolyzable ether or ester group by hydrogenation in the manner described in connection with the conversion of a compound of formula II to a compound of formula XI. If desired, where $R_8'$ is a protected hydroxy group in the compound of formula XVI, the hydroxy group can be regenerated by hydrolysis as described above in the conversion of a compound of formula XIV to a compound of formula X. The compounds of formula XVI which are novel compounds are those compounds where $R_1$ is lower alkyl.

The compound of formula XIV and the compound of formula XVI where $R_8'$ is a protected hydroxy group can be converted into a compound of the formula I-A where $R_2$ and $R_3$ form an oxo group via the following intermediate:

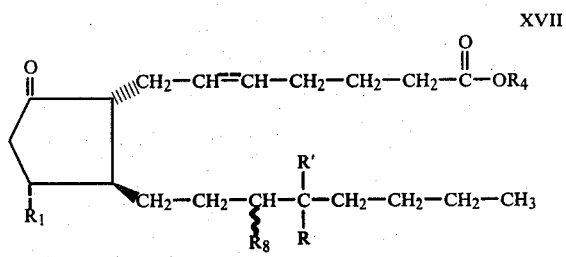

wherein $R_1$, $R_4$, $R_8$, R and R' are as above; and the dotted bond is optionally hydrogenated.

The compound of formula XIV and the compound of formula XVI are oxidized to the compound of formula XVII by treating the compound of formula XIV and the compound of formula XVI where $R_8'$ is a protected hydroxy group with an oxidizing agent. Any conventional oxidizing agent capable of oxidizing a hydroxy group to a keto group can be utilized for this conversion. Among the preferred oxidizing agents are included the chromate oxidizing agents such as chromium trioxide. Any of the conditions conventional in oxidizing with these agents can be used in this conversion. The compound of formula XVII can be converted to the compound of formula I-A where A and B are hydrogen by hydrolysis of the protecting group $R_8$ in the manner described in connection with the conversion of a compound of the formula XIV to a compound of the formula X.

The compound of formula I-B where A and B form a carbon to carbon bond is prepared from a compound of the formula:

wherein $R_1$, $R_2$, $R_3$, $R_4$, R and R' are as above and the dotted bond can be optionally hydrogenated by oxidation.

The compound of formula XX is the compound of formula I in Ser. No. 745,257 filed Dec. 8, 1976. The preparation of this compound is disclosed in Ser. No. 745,257 which disclosure is incorporated herein by reference. This oxidation is accomplished in the same manner as disclosed hereinbefore in connection with the oxidation of the compounds of formula XIV and XVI to a compound of formula XVII.

The compound of formula I-B where A and B are hydrogen is prepared from the compound of formula I-A where $R_2$ and $R_3$ are oxo, i.e. a compound of the formula

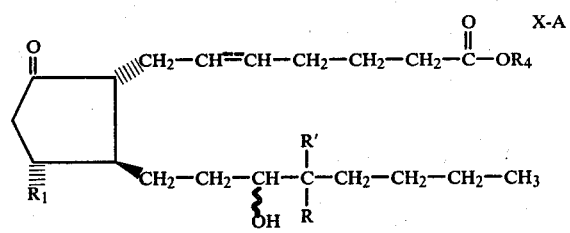

wherein $R_1$, $R_4$, R and R' are as above, and the dotted bond can be optionally hydrogenated by oxidation such as described hereinbefore in connection with the oxidation of a compound of formula XIV.

The invention is illustrated by the following examples. In the examples, the ether is diethyl ether. All temperatures are in degrees centigrade. Jones reagent is 2.4-molar solution of chromium trioxide in sulfruic acid. HMPA as used in the examples is hexamethyl phosphoramide.

EXAMPLE 1 nat
11R-methyl-16R-fluoro-9,15-dioxoprosta-5(Z),13(E)-dienoic acid

To a solution of 100 mg of nat 11R-methyl-16R-fluoro-15R-hydroxy-9-oxoprosta-5(Z),13(E)-dienoic acid or nat 11R-methyl-16R-fluoro-15S-hydroxy-9-oxoprosta-5(Z),13(E)-dienoic acid in 10 ml of a 5:1 parts by volume diethylether acetone solution there was added 0.15 ml of Jones reagent. After thirty minutes, the reaction was worked up by adding 50 ml of ether. The solution was then washed with dilute aqueous sodium chloride solution. The organic layer was dried (MgSO$_4$) and the solvent removed under reduced pressure. The crude product was purified by silica gel chromatography to give 80 mg of nat 11R-methyl-16R-fluoro-9,15-dioxoprosta-5(Z),13(E)-dienoic acid as a colorless liquid, $[\alpha]_D^{25} -13°$ (EtOH).

Anal. Calcd. for $C_{21}H_{31}FO_4$: Calcd. C 68.83, H 8.52. Found C 68.60, H 8.58.

EXAMPLE 2 nat 11R-Methyl-16S-fluoro-9,15-dioxoprosta-5(Z),13(E)-dienoic acid

By the procedure of example 1, 11R-methyl-16S-fluoro-15R-hydroxy-9-oxoprosta-5(Z),13(E)-dienoic acid was converted to nat 11R-methyl-16S-fluoro-9,15-dioxoprosta-5(Z),13(E)—dienoic acid.

EXAMPLE 3 nat 16R-Fluoro-9,15-dioxoprosta-5(Z),13(E)-dienoic acid

By the procedure of example 1, nat-16R-fluoro-15R-hydroxy-9-oxoprosta-5(Z),13(E)-dienoic acid was converted to nat-16R-fluoro-9,15-dioxoprosta-5(Z),13(E)-dienoic acid, a colorless oil.

Mass spec M+(m/e 352);
UV (EtOH) λ max 238 nm ($\epsilon = 10600$).

EXAMPLE 4 nat 16R-Trifluoromethyl-9,15-dioxoprosta-5(Z),13(E)-dienoic acid

By the procedure of example 1, nat-16R-trifluoromethyl-15R-hydroxy-9-oxoprosta-5(Z),13(E)-dienoic acid was converted to nat-16R-trifluoromethyl-9,15-dioxoprosta-5 (Z),13-(E)-dienoic acid.

EXAMPLE 5 nat 11R,16,16-Trimethyl-9,15-dioxoprosta-5(Z),13(E)-dienoic acid

By the procedure of example 1, nat-11R,16,16-trimethyl-15R-hydroxy-9-oxoprosta5-(Z),13-(E)-dienoic acid was converted to nat-11R,16,16-trimethyl-9,15-dioxoprosta-5(Z),13-(E)-dienoic acid; a colorless oil.

Mass spec. M+(m/e 376)
U.V. (EtOH) λ max 235 nm ($\epsilon = 7425$)

EXAMPLE 6 nat 3,3aR,4,5,6,6aS-Hexahydro-4R(4R-fluoro-3R-hydroxyoctanyl)-5R-methyl-2H-cyclopenta[b]furan-2-one A mixture of 1 g of 3,3aR,4,5,6,6aS-hexahydro-4R[4R-fluoro-3-R-hydroxy-1-(E)-octenyl]-5R-methyl-2H-cyclopenta[b]furan-2-one, 100 mg of pre-reduced $PtO_2$ and 75 ml of ethyl acetate was hydrogenated at room temperature and atmospheric pressure until the theoretical uptake of hydrogen was realized. The mixture was then filtered and the solvent removed under reduced pressure. Trituration of the residue with hexane afforded 700 mg of 3,3aR,4,5,6,6aS-hexahydro-4R[4R-fluoro-3R-hydroxy-octanyl]-5-R-methyl-2H-cyclopenta[b]furan-2-one, mp. 52°–55°.

EXAMPLE 7

3,3aR,4,5,6,6aS-Hexahydro-4R[4R-fluoro-3R-[2-tetrahydro-(2H)-pyranyloxy]-octanyl]5R-methyl-2H-cyclopenta-[b]furan-2-ol To a solution of 730 mg of 3,3aR,4,5,6,6aS-hexahydro-4R-(4R-fluoro-3R-hydroxyoctanyl)-5R-methyl-2H-cyclopenta[b]furan-2-one in 50 ml of methylene chloride, there was added 50 mg of para-toluene sulfonic acid and one ml of dihydropyran. The solution was stirred at room temperature for three hours. To the resulting solution, there was then added 10 drops of a saturated aqueous sodium bicarbonate solution followed by 200 ml of ether. The organic layer was then washed with a saturated aqueous sodium chloride solution, dried (MgSO4) and the solvents removed under reduced pressure. Purification of the residue was carried out via chromatography to give 3,3aR,4,5,6,6aS-hexahydro4R-[4R-fluoro-3R-[2-tetrahydro-(2H)-pyranyloxy]-octanyl]5R-methyl-2H-cyclopenta[b]furan-2-one. This crude product was dissolved in 10 ml of dry toluene and treated under argon at −70° with 2 ml of a 1.5 N solution of diisobutyl aluminum hydride in toluene. After 1 hr., methanol was slowly added and the reaction warmed to room temperature, then followed the addition of 2 ml of water. The mixture was then filtered through celite and the solvent removed under reduced pressure to give, after chromatography, 3,3aR,4,5,6,6aS-hexahydro-4R[4R-fluoro-3R-[2-tetrahydro-(2H)-pyranyloxy]-octanyl]-5R-methyl-2H-cyclopenta-[b]furan-2-ol as a thick colorless oil:

Mass spectrum m/e 372, 354, 269.

EXAMPLE 8 nat 11R-Methyl-16R-fluoro-15R-[2-tetrahydro-(2H)-pyranyloxy]9S-hydroxyprost5(Z)-enoic acid Sodium bis (trimethylsilyl) amide (4.8 g) was dissolved in 50 ml of HMPA while a stream of argon was continually bubbling thru the solution. (4-Carboxy butyl)-triphenylphosphonium bromide (5.8 g) was then added and the slurry stirred until a deep red solution was formed. To this solution was then added 2 g of 3,3aR,4,5,6,6aS-hexahydro-4R[4R-fluoro-3R-(tetrahydro-(2H)-2-pyranyloxy)-octanyl]-5R-methyl-2H-cyclopenta-[b]-furan-2-ol dissolved 20 ml of HMPA. The resulting solution was stirred at room temperature for 15 min. followed by the dropwise addition of 1 ml of glacial acetic acid until the solution became straw colored. The HMPA was then removed under high vacuum. To the residue was then added 55 ml of 1 N sodium hydroxide and the mixture stirred for 18 hr. The precipitate was then filtered and the aqueous solution made acidic with dilute hydrochloric acid. The resulting mixture was then extracted with ether, the ether solution dried (Na2SO4) and the solvent removed under vacuum. Chromatography of the residue afforded 2.4 g of nat 11R-methyl-16R-fluoro-15R-[2-tetrahydro-(2H)-pyranyloxy]-9S-hydroxyprost5(Z)-enoic acid as a thick colorless oil:

Mass spectrum m/e 456,438

EXAMPLE 9 nat 11R-Methyl-16R-fluoro-15R-hydroxy-9-oxoprost-5-(Z)-enoic acid

To a rapidly stirred solution of 838 mg of nat. 11R-methyl-16R-fluoro-15R-[2-tetrahydro(2H)-pyranyloxy]-9S-hydroxyprost-5(Z)-enoic acid in 100 ml of ether-acetone (5:1) was added at 0° with stirring 0.6 ml of Jones reagent. After 10 min., several drops of isopropanol was added followed after several minutes by the addition of 1.5 g of sodium bicarbonate and 5 ml of water. 100 ml of ether was then added to the mixture which was then filtered and the organic layer washed with sat. sodium chloride solution. The ether solution was then dried and the solvent removed under reduced pressure to give crude nat. 11R-methyl-16R-fluoro-15R-[2-tetrahydro-(2H)-pyranyloxy]-9-oxoprost-5(Z)-enoic acid. This crude material (750 mg) was then dissolved in 15 ml of a 5:1 acetic acid-water solution and heated at 49° for 1.5 hr. The solvent was then removed under high vacuum and the residue purified by chromatography to give 400 mg of nat. 11R-methyl-16R-fluoro-15R-hydroxy-9-oxoprost-5-(Z)-enoic acid a thick colorless oil:

Mass spectrum m/e 370, 352, 332

EXAMPLE 10 nat 11R-Methyl-16R-fluoro-9,15-dioxoprost-5(Z)-enoic acid

To a solution of nat. 11R-methyl-16R-fluoro-15R-hydroxy-9-oxoprost-5-(Z)-enoic acid (600 mg) dissolved in 50 ml of 5:1 parts by volume ether; acetone solution was added Jones reagent. After the usual work up as in Example 1, pure nat. 11R-methyl-16R-fluoro-9,15-dioxoprost-5(Z)-enoic acid was obtained via chromatography as a thick colorless oil:

Mass spectrum m/e 386,350,348

EXAMPLE 11

3,3aR,4,5,6,6aS-Hexahydro-4R(4R-fluoro-3S-hydroxy-octanyl)-5R-methyl-2H-cyclopenta [b]furan-2-one By the procedure of example 6, 3,3aR,4,5,6,6aS-hexahydro-4R[4R-fluoro-3S-hydroxy-1-(E)-octenyl]-5R-methyl-2H-cyclopenta[b]furan-2-one was converted to 3,3aR,4,5,6,6aS—hexahydro-4R(4R-fluoro-3S-hydroxy-octanyl)-5R-methyl-2H-cyclopenta[b]furan-2-one, a thick colorless oil:

Mass spectrum m/e 286,268,248,197,179

EXAMPLE 12

3,3aR,4,5,6,6aS-Hexahydro-4R[4R-fluoro-3S-[2-tetrahydro-(2H)-pyranyloxy]-octanyl]-5R-methyl-2H-cyclopenta-[b]-furan-2-ol By the same procedure of Example 7, 3,3aR,4,5,6,6aS-hexahydro-4R-(4R-fluoro-3S-hydroxy-octanyl)-5R-methyl-2H-cyclopenta-[b]-furan-2-one was converted to 3,3aR,4,5,6,6aS-hexahydro-4R-[4R-fluoro-3S-[2-tetrahydro-(2H)-pyranyloxy]-octanyl]-5R-methyl-2H-cyclopenta-[b]-furan-2-ol as a thick colorless oil:

Mass spectrum m/e 372, 354, 269.

EXAMPLE 13 nat. 11R-Methyl-16R-fluoro-15S-[2-tetrahydro-(2H)-pyranyloxy]-9S-hydroxyprost-5(Z)-enoic acid By the same procedure of Example 8, 3,3aR,4,5,6,6aS-hexahydro-4R-[4R-fluoro-3S-[2-tetrahydro-(2H)-pyranyloxy]-octanyl]-5R-methyl-2H-cyclopenta-[b]-furan-2-ol was converted to nat. 11R-methyl-16R-fluoro-15S-[2-tetrahydro-(2H)-pyranyloxy]-9S-hydroxyprost-5(Z)-enoic acid as a thick colorless oil:

Mass spectrum m/e 456, 438.

EXAMPLE 14 nat 11R-Methyl-16R-fluoro-15S-hydroxy-9-oxoprost-5(Z)-enoic acid

By the procedure of example 9, nat. 11R-methyl-16R-fluoro-15S-[2-tetrahydro-(2H)-pyranyloxy]9S-hydroxyprost-5(Z)-enoic acid was converted to nat. 11R-methyl-16R-fluoro-15S-hydroxy-9-oxoprost-5(Z)-enoic acid, a thick colorless oil: mass spectrum m/e 370, 352.

EXAMPLE 15 nat. 11R-methyl-16,16-difluoro-9,15-dioxoprosta-5(Z).13(E)-dienoic acid

By the procedure of example 1, nat 11R-methyl-16,16-difluoro-15R-hydroxy-9-oxoprosta-5(Z)-13(E)-dienoic acid was converted to nat 16,16-difluoro-9,15-dioxoprosta-5(Z),13(E)-dienoic acid.

EXAMPLE 16

3,3aR,4,5,6,6aS-Hexahydro-4R-(4,4-dimethyl-3R-hydroxy-octanyl)-2H-cyclopenta[b]furan 2-one By the procedure of example 6, 3,3aR,4,5,6,6aS-hexahydro-4R-[4,4-dimethyl-3-R-hydroxy-1-(E)-octenyl]-2H-cyclopenta[b]furan-one was hydrogenated to give 3,3aR,4,5,6,6aS-hexahydro-4R-(4,4-dimethyl-3R-hydroxy-octanyl)-2H-cyclopenta[b]furan-2-one.

EXAMPLE 17

3,3aR,4,5,6,6aS-Hexahydro-4R-(4R-methyl-4R-trifluoromethyl-3R-hydroxy-octanyl)-5R-methyl-2H-cyclopenta[b]furan-2-one By the procedure of example 6, 3,3aR,4,5,6,6aS-hexahydro-4R-[4R-methyl-4R-trifluoromethyl-3R-hydroxy-1-(E)-octenyl]-5R-methyl-2H-cyclopenta[b]furan-2-one was hydrogenated to give 3,3aR,4,5,6,6aS-hexahydro-4R-(4R-methyl-4R-trifluoromethyl-3R-hydroxy-octanyl)-5R-methyl-2H-cyclopenta[b]furan-2-one.

EXAMPLE 18

3,3aR,4,5,6,6aS-Hexahydro-4R-(4R-trifluoromethyl-4R-fluoro-3R-hydroxyoctanyl)-5R-methyl-2H-cyclopenta[b]furan-2-one By the procedure of example 6, 3,3aR,4,5,6,6aS-hexahydro-4R-[4R-trifluoromethyl-4R-fluoro-3R-hydroxy-1-(E)-octenyl]-5R-methyl-2H-cyclopenta[b]furan-2-one was hydrogenated to give 3,3aR,4,5,6,6aS-hexahydro-4R-(4R-trifluoromethyl-4R-fluoro-3R-hydroxy-octanyl)-5R-methyl-2H-cylopenta[b]furan-2-one.

EXAMPLE 19

3,3aR,4,5,6,6aS-Hexahydro-4R-[4,4-dimethyl-3R-[2-tetrahydro-(2H)-pyranyloxy]octanyl]-2H-cyclopenta[b]furan-2-ol By the procedure of example 7, 3,3aR,4,5,6,6aS-hexahydro-4R-(4,4-dimethyl-3R-hydroxyoctanyl)-2H-cyclopenta[b]furan-2-one was converted to 3,3aR,4,5,6,6aS-hexahydro-4R-[4,4-dimethyl-3R-[2-tetrahydro-(2H)-pyranyloxy]octanyl]-2H-cyclopenta[b]furan-2-ol.

EXAMPLE 20

3,3aR,4,5,6,6aS-Hexahydro-4R-[4R-methyl-4R-trifluoromethyl-3R-[2-tetrahydro-(2H)-pyranyloxy]octanyl]-5R-methyl-2H-cyclopenta[b]furan-2-ol By the procedure of example 7, 3,3aR,4,5,6,6aS-hexahydro-4R-(4R-methyl-4R-trifluoromethyl-3R-hydroxyoctanyl)-5R-methyl-2H-cyclopenta[b]furan-2-one was converted to 3,3aR,4,5,6,6aS-hexahydro-4R-[4R-methyl-4R-trifluoromethyl-3R-[2-tetrahydro-(2H)- pyranyloxy]-octanyl]-5R-methyl-2H-cyclopenta[b]furan-2-ol.

EXAMPLE 21

3,3aR,4,5,6,6aS-Hexahydro-4R-[4R-trifluoromethyl-4R-fluoro-3R-[2-tetrahydro-(2H)-pyranyloxy]-octanyl]-5R-methyl-2H-cyclopenta[b]furan-2-ol By the procedure of example 7, 3,3aR,4,5,6,6aS-hexahydro-4R-(4R-trifluoromethyl-4R-fluoro-3R-hydroxy-octanyl)-5R-methyl-2H-cyclopenta[b]furan-2-one was converted to 3,3aR,4,5,6,6aS-hexahydro-4R-[4R-trifluoromethyl-4R-fluoro-3R-[2-tetrahydro-(2H)-pyranyloxy]-octanyl]-5R-methyl-2H-cyclopenta[b]furan-2-ol.

EXAMPLE 22

16,16-Dimethyl-9S-hydroxy-15R-[2-tetrahydro-(2H)-pyranyloxy]-prost-5-(Z)-enoic acid By the procedure of example 8, 3,3aR,4,5,6,6aS-hexahydro-4R-[4,4-dimethyl-3R-[2-tetrahydro-(2H)-pyranyloxy]octanyl]-2H-cyclopenta[b]furan-2-ol was converted to nat. 16,16-dimethyl-9S-hydroxy-15R-[2-tetrahydro-(2H)-pyranyloxy]-prost-5-(Z)-enoic acid.

EXAMPLE 23

16R-Trifluoromethyl-16R,11R-dimethyl-15R-[2-tetrahydro-(2H)-pyranyloxy]-9S-hydroxyprost-5-(Z)-enoic acid By the procedure of example 8, 3,3aR,4,5,6,6aS-hexahydro-4R-[4R-methyl-4R-trifluoromethyl-3R-[2-tetrahydro-(2H)-pyranyloxy]octanyl]-5R-methyl-2H-cyclopenta[b]furan-2-ol was converted to nat. 16R-trifluoromethyl-16R-11R-dimethyl-15R-[2-tetrahydro-(2H)-pyranyloxy]-9S-hydroxyprost-5-(Z)-enoic acid.

EXAMPLE 24

16R-Trifluoromethyl-16R-fluoro-15R-[2-tetrahydro-(2H)-pyranyloxy]-11R-methyl-9S-hydroxyprost-5-(Z)-enoic acid By the procedure of example 8, 3,3aR,4,5,6,6aS-hexahydro-4R-[4R-trifluoromethyl-4R-fluoro-3R-[2-tetrahydro-(2H)-pyranyloxy]octanyl]-5R-methyl-2H-cyclopenta[b]furan-2-ol was converted to nat. 16R-trifluoromethyl-16R-fluoro-15R-[2-tetrahydro-(2H)-pyranyloxy]-11R-methyl-9S-hydroxyprost-5-(Z)-enoic acid.

EXAMPLE 25 nat 16,16-Dimethyl-15R-hydroxy-9-oxoprost-5(Z)-enoic acid

By the procedure of example 9, nat 16,16-dimethyl-9S-hydroxy-15R-[2-tetrahydro-(2H)-pyranyloxy]prost-5(Z)-enoic acid was converted to nat 16,16-dimethyl-15R-hydroxy-9-oxoprosta-5(Z)-enoic acid.

EXAMPLE 26 nat 16R-Trifluoromethyl-16R,11R-dimethyl-15R-hydroxy-9-oxoprost-5(Z)-enoic acid

By the procedure of example 9, nat 16R-trifluoromethyl-16R,11R-dimethyl-15R-[2-tetrahydro-(2H)-pyranyloxy]-9S-hydroxyprost-5(Z)-enoic acid was converted to nat 16R-trifluoromethyl-16R,11R-dimethyl-15R-hydroxy-9-oxoprost-5(Z)-enoic acid.

EXAMPLE 27 nat 16R-Trifluoromethyl-16R-fluoro-15R-hydroxy-11R-methyl-9-oxoprost-5(Z)-enoic acid By the procedure of example 9, nat 16R-trifluoromethyl-16R-fluoro-15R-[2-tetrahydro-(2H)-pyranyloxy]-11R-methyl-9S-hydroxyprost-5(Z)-enoic acid was converted to nat 16R-trifluoromethyl-16R-fluoro-15R-hydroxy-11R-methyl-9-oxoprost-5(Z)-enoic acid.

EXAMPLE 28 nat 16,16-Dimethyl-9,15-dioxoprost-5(Z)-enoic acid

By the procedure of example 10, nat 16,16-dimethyl-15R-hydroxy-9-oxoprost-5(Z)-enoic acid was converted to nat 16,16-dimethyl-9,15-dioxoprost-5(Z)-enoic acid.

EXAMPLE 29 nat 16R-Trifluoromethyl-16R,11R-dimethyl-9,15-dioxoprost-5(Z)-enoic acid

By the procedure of example 10, nat 16R-trifluoromethyl-16R,11R-dimethyl-15R-hydroxy-9-oxoprost-5(Z)-enoic acid was converted to nat 16R-trifluoromethyl-16R,11R-dimethyl-15,9-dioxoprost-5(Z)-enoic acid.

EXAMPLE 30 nat 16R-Trifluoromethyl-16R-fluoro-11R-methyl-9,15-dioxoprost-5(Z)-enoic acid

By the procedure of example 10, nat 16R-trifluoromethyl-16R-fluoro-15R-hydroxy-11R-methyl-9-oxoprost-5(Z)-enoic acid was converted to nat 16R-trifluoromethyl-16R-fluoro-11R-methyl-9,15-dioxoprost-5(Z)-enoic acid.

EXAMPLE 31 nat 11R-methyl-16R-fluoro-9S,15R-dihydroxy prost-5(Z)-enoic acid nat 11R-methyl-16R-fluoro-15R-[2-tetrahydro-(2H)-pyranyloxy]-9S-hydroxy-prost-5(Z)-enoic acid (500 mg) was warmed at 40° C. for 18 hrs. with 50 ml of a mixture of acetic acid-water-tetrahydrofuran (55-30-15 parts by volume). After this time, the solvent was evaporated at reduced pressure and the residual oil purified by column chromatography on silica gel using 0–60% ethyl acetate/benzene as the eluent to give 400 mg (97%) of nat 11R-methyl-16R-fluoro-9S,15R-dihydroxy-prosta-5(Z)-enoic acid as a colorless oil.

EXAMPLE 32

By the procedure of example 31, nat 16,16-dimethyl-9S-hydroxy-15R-[2-tetrahydro-(2H)-pyranyloxy]-prost-5(Z)-enoic acid was converted to nat 16,16-dimethyl-9S,15R-dihydroxy-prost-5(Z)-enoic acid.

EXAMPLE 33

A tablet was prepared containing the following ingredients:

| | Per Tablet |
|---|---|
| nat 11R-methyl-16R-fluoro-9,15-dioxoprosta- | |

| | Per Tablet |
|---|---|
| 5(Z),13(E)-dienoic acid | 200 mg. |
| Dicalcium phosphate dihydrate, unmilled | 235 mg. |
| Corn Starch | 70 mg. |
| FD&C Yellow #5 - Aluminum Lake 25% | 2 mg. |
| Durkee Duratex* | 25 mg. |
| Calcium Stearate | 3 mg. |
| Total Weight | 535 mg. |

*Hydrogenated cotton seed oil (fully saturated)

All of the above ingredients were mixed until thoroughly blended in a suitable size container. The powder was filled into #2, two-piece, hard-shell gelatin capsules to an approximate fill weight of 350 mg using a capsulating machine.

EXAMPLE 34

A capsule was prepared by the procedure of example 33 except that nat 11R-methyl-16R-fluoro-15S-hydroxy-9-oxoprost-5(Z)-enoic acid was the active ingredient.

EXAMPLE 35

A capsule was prepared by the procedure of example 33 except nat 16R-trifluoromethyl-16R-fluoro-15R-hydroxy-11R-methyl-9-oxoprost-5(Z)-enoic acid was the active ingredient.

EXAMPLE 36

A tablet was found containing:

| | Per Tablet |
|---|---|
| nat 11R-methyl-16R-fluoro-9,15-dioxoprosta-5(Z),13(E)-dienoic acid | 25 mg. |
| Dicalcium phosphate dihydrate, unmilled | 175 mg. |
| Corn Starch | 24 mg. |
| Magnesium stearate | 1 mg. |
| Total Weight | 225 mg. |

The active ingredient and corn starch were mixed together and passed through a #00 screen in Model "J" Fitzmill with hammers forward. This premix was the mixed with dicalcium phosphate and one-half of the magnesium stearate, passed through a #1A screen in Model "J" Fitzmill with knives forward, and slugged. The slugs were passed through a #2A plate in a Model "D" Fitzmill at slow speed with knives forward and the remaining magnesium stearate was added. The mixture was mixed and compressed.

EXAMPLE 37

A tablet was formulated in the same manner as in Example 36 except that nat 16R-trifluoromethyl-16R-fluoro-15R-hydroxy-11R-methyl-9-oxoprost-5(Z)-enoic acid was the active ingredient.

EXAMPLE 38

A tablet was formulated in the same manner as in example 36 except nat 11R-methyl-16R-fluoro-15S-hydroxy-9-oxoprost-5(Z)-enoic acid was the active ingredient.

We claim:

1. A compound of the formula:

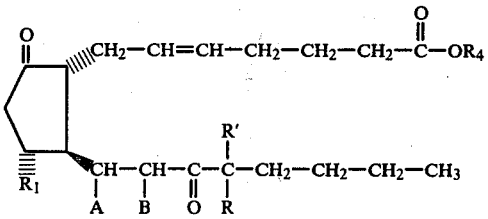

wherein A and B are individually hydrogen; $R_4$ is hydrogen or lower alkyl; $R_1$ is lower alkyl; $R'$ is fluoro, lower alkyl or trifluoromethyl; R is hydrogen, fluoro, or lower alkyl;

or their optical antipodes or racemates thereof.

2. The compound of claim 1 wherein said compound is nat 16R-trifluoromethyl-16R,11R-dimethyl-9,15-dioxoprost-5(Z)-enoic acid.

3. The compound of claim 1 wherein said compound is nat 16R-trifluoromethyl-16R-fluoro-11R-methyl-9,15-dioxoprost-5(Z)-enoic acid.

4. The compound of claim 1 wherein said compound is nat 11R-methyl-16R-fluoro-9,15-dioxoprost-5(Z)-enoic acid.

* * * * *